US006883787B2

(12) United States Patent
Allen

(10) Patent No.: US 6,883,787 B2
(45) Date of Patent: Apr. 26, 2005

(54) PAPER TOWEL DISPENSER WITH DEODORIZER

(75) Inventor: Charles S. Allen, Kenilworth, IL (US)

(73) Assignee: Sloan Valve Company, Franklin Park, IL (US)

( * ) Notice: Subject to any disclaimer, the term of this patent is extended or adjusted under 35 U.S.C. 154(b) by 185 days.

(21) Appl. No.: 10/288,879

(22) Filed: Nov. 6, 2002

(65) Prior Publication Data

US 2004/0084550 A1 May 6, 2004

(51) Int. Cl.[7] .............. B01D 47/00; F02M 37/00; F02M 69/02; A24F 25/00; A61L 9/04
(52) U.S. Cl. .................. 261/30; 261/DIG. 88; 239/52; 239/289; 422/124
(58) Field of Search ............ 239/52, 34, 53–55, 239/60, 326, 289; 242/595.1, 905; 261/DIG. 88, 30; 428/905; 422/124

(56) References Cited

U.S. PATENT DOCUMENTS

| 2,347,591 A | | 4/1944 | Cohn | |
|---|---|---|---|---|
| 2,539,059 A | | 1/1951 | Cohn | |
| 2,639,939 A | * | 5/1953 | Matchett | 242/599.3 |
| 2,746,798 A | | 5/1956 | Wardell, Jr. | |
| 2,806,738 A | * | 9/1957 | Tsakalas | 239/52 |
| 2,901,790 A | * | 9/1959 | Nielsen | 422/123 |
| 3,192,008 A | | 6/1965 | Dwyer | |
| 4,436,224 A | | 3/1984 | McInerny | |
| 4,770,679 A | | 9/1988 | Slaughter | |
| 4,925,102 A | * | 5/1990 | Jones et al. | 239/52 |
| 5,170,938 A | * | 12/1992 | Dewing | 239/52 |
| 5,312,021 A | | 5/1994 | Nelson | |
| 5,381,984 A | | 1/1995 | Hindsgual | |
| 6,000,658 A | * | 12/1999 | McCall, Jr. | 242/599 |
| 6,425,530 B1 | * | 7/2002 | Coakley | 239/52 |
| 6,575,383 B1 | * | 6/2003 | Dobler et al. | 239/52 |
| 6,688,551 B1 | | 2/2004 | He et al. | |

FOREIGN PATENT DOCUMENTS

| EP | 0 313 215 A3 | 4/1989 |
|---|---|---|
| GB | 618311 | 2/1949 |
| GB | 2 367 548 A | 4/2002 |

* cited by examiner

Primary Examiner—Steven J. Ganey
Assistant Examiner—Darren Gorman
(74) Attorney, Agent, or Firm—Cook, Alex, McFarron, Manzo, Cummings & Mehler, Ltd.

(57) ABSTRACT

A deodorizing paper towel dispenser includes a housing, with a paper towel roll mounted within the housing for rotation. There may be a drive within the housing which is connected to rotate the paper towel roll. The drive means can be activated either by an infrared sensor or by a manual switch. The paper towel roll includes a generally hollow core and a deodorant associated with the core. A fan is positioned to pass air through the paper towel roll core and outwardly through an opening in the housing. The fan is operated by a drive that rotates with the paper towel roll.

5 Claims, 1 Drawing Sheet

PAPER TOWEL DISPENSER WITH DEODORIZER

THE FIELD OF THE INVENTION

The present invention relates to a paper towel dispenser which includes a concurrently operated bathroom deodorizer. It is current practice, if there is to be a deodorizer in a public washroom, that it be a separate device, separately maintained from other washroom fixtures. Each fixture that is mounted in a public washroom requires maintenance and if there is an excessive number of such fixtures, the washroom facility takes on a somewhat cluttered appearance. The present invention combines a deodorizer and a paper towel dispenser, with the deodorizer being activated whenever the paper towel dispenser is utilized by a user of the washroom facility.

More specifically, the paper towel dispenser will include the conventional semi-perforated paper towels or a continuous roll that requires a device to dispense a towel to the user wound about a core, often made of cardboard. The core may have the deodorizer impregnated within it or the deodorant may be applied on the inside of the core, as a coating, or it may be in the form of individual particles or a cake positioned within the core. In any such event, the deodorant will be dispensed into the adjoining area by a fan, which will pass air through the core, with the fan being operated by the drive motor which functions to dispense paper towels or by a manually actuated drive mechanism which is powered by a user.

SUMMARY OF THE INVENTION

The present invention relates to a deodorizing paper towel dispenser and to a paper towel roll which has an integral deodorant within the roll core.

A primary purpose of the invention is to provide a paper towel dispenser in which a deodorant is concurrently dispensed into the adjoining area whenever towels are dispensed.

Another purpose of the invention is to provide a paper towel dispenser as described in which the deodorant is integral with the paper towel roll core.

Another purpose of the invention is to provide a paper towel dispenser with a built-in deodorant and in which whenever a paper towel is dispensed by operation of the paper towel drive motor, which is actuated either by a manual switch or by infrared operation, or by a manual drive operated by pulling of a towel, a fan will concurrently pass air through the deodorant associated with the paper towel roll.

Other purposes will appear in the ensuing specification, drawings and claims.

BRIEF DESCRIPTION OF THE DRAWINGS

The invention is illustrated diagrammatically in the attached illustrations of a deodorant dispensing paper towel dispenser.

DESCRIPTION OF THE PREFERRED EMBODIMENTS

There are known paper towel dispensers which may include a deodorant. For example, U.S. Pat. No. 3,192,008 discloses a paper towel dispenser in which a fan blows air over a cake of deodorant into the area surrounding the dispenser, with the cake of deodorant being disassociated from the paper towel roll.

U.S. Pat. No. 2,746,798 illustrates a toilet paper roll having a liquid deodorant which is sprayed whenever the roll is turned.

U.S. Pat. No. 2,539,059 illustrates another form of paper towel dispenser in which a fan, separate from the paper towel roll, blows air over a deodorant, separate from the paper towel roll.

U.S. Pat. No. 2,347,591 illustrates a vapor diffusing device in which a fan blows air over a cake of deodorant.

U.S. Pat. No. 4,436,224 illustrates a paper towel roll in which a deodorant is positioned within the center of the vertically oriented core of the roll and is dispensed by the operation of a manually operated pump located in the core.

Public washrooms commonly have hand washing devices such as faucets, and in addition, hand drying fixtures, which may include air dryers, paper towels located in a stack, a cloth device which is dispensed by pulling on a portion of the cloth, and paper towel rolls which are in the form of a continuous roll. In addition, it is common in public washrooms to now have a deodorizer, normally a unit which is separate from any type of hand drying device. Each fixture in a public washroom requires maintenance and installation. The present invention combines a hand drying device and a deodorant dispensing device so as to reduce the cost of maintenance in a public washroom and to reduce the cost of initially installing fixtures. A paper towel dispenser, in the form of a continuous roll, includes a core which has a deodorant located within it. The generally hollow core is in alignment with a fan and the fan is operated whenever the paper towel dispenser roll is rotated so that deodorized air passes from the core of the paper towel roll whenever a user takes a towel.

Sloan Valve Company of Franklin Park, Ill., the assignee of the present application, has been a pioneer in the manufacture and sale of infrared controlled plumbing devices such as toilet room flush valves, faucets and the like. U.S. Pat. No. 5,548,119 is illustrative of a toilet room sensor assembly which has utility with such products. The disclosure of the '119 patent is herein incorporated by reference.

Figure 1:
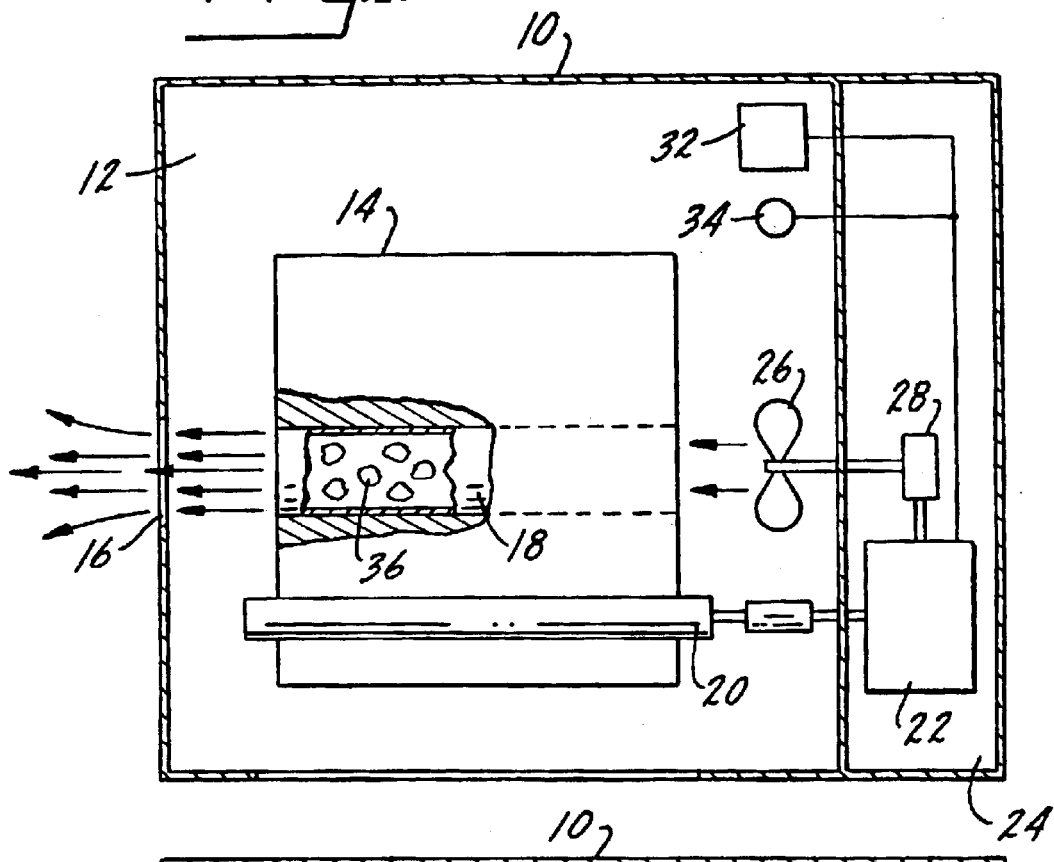
FIG. 1 is a front elevational view of an electric motor driven towel dispenser.

In FIG. 1 of the drawings, a housing is indicated at 10 and may have a compartment 12 within which is positioned a paper towel roll 14. There will be a slot or aperture through which the towels will pass to the user. There is an opening 16 in the housing 10 which is in alignment with the core 18 of the roll 14. The roll 14 may be rotated by an idler roller 20, driven by a drive motor 22 positioned within a compartment 24 of the housing 10. The drive motor 22 will also rotate a fan 26 through a mechanical drive connection 28. The fan is in alignment with the core 18 and with the opening 16 such that when the motor 22 drives the roller 20 to rotate the paper towel roll 14, air will be passed through the core 18 and out of the opening 16.

Alternate forms of activation for the drive motor 22 are illustrated in FIG. 1 of the drawings. An infrared sensor of the type shown in the '119 patent, or of a similar type, is indicated at 32 and may be connected by wires to the drive 22. Power for the unit may either be supplied by conventional electric power or by battery. There is also a manual switch 34 which may function either as an override device, in the event the infrared sensor is inoperable, or as a separate means to operate the paper towel dispenser.

The core 18, which may conventionally be made of cardboard, may have a suitable deodorant impregnated within the core. In an alternate form of the invention, deodorant granules 36 may be positioned within the generally hollow core 18 such that when air is blown over the granules, deodorized air will pass through the opening 16. Similarly, if the core 18 is impregnated with a suitable deodorant, deodorized air will also pass through the core and out the opening 16 when the fan 26 is driven by motor 22. The core 18 may, in further embodiments of the invention, include a film of deodorant on the wall of the core, or a cake may be positioned in the core.

Figure 2:
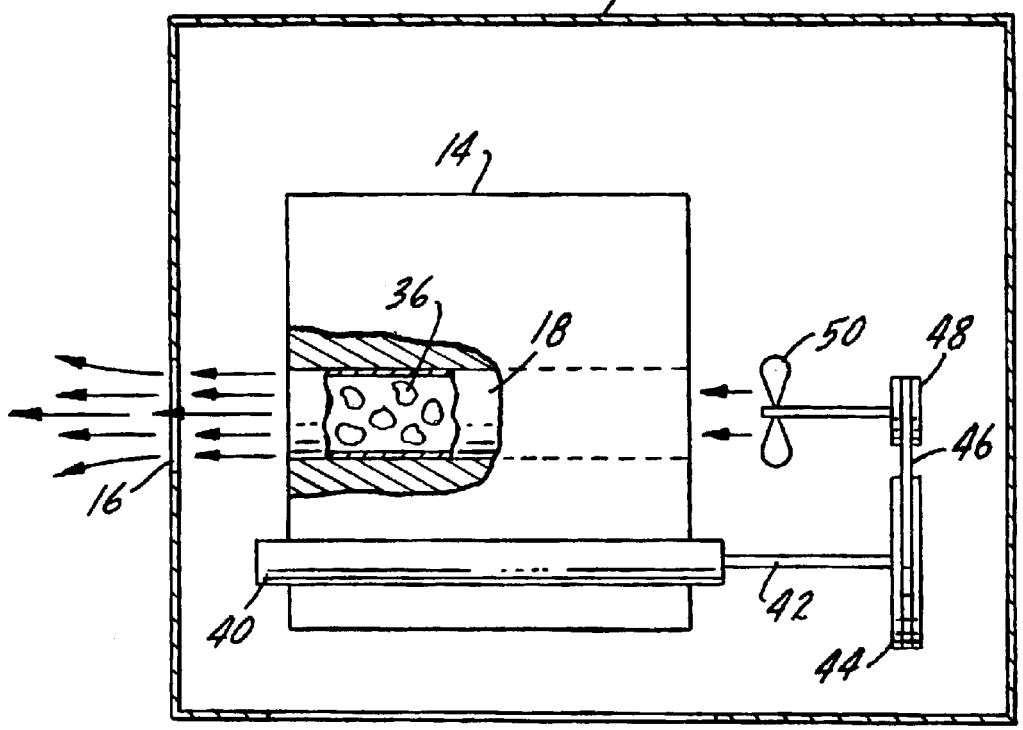
FIG. 2 is a front elevational view of a manually actuated paper towel dispenser.

A second embodiment of the deodorizing paper towel dispenser of the invention is shown in FIG. 2 of the drawings. This embodiment includes a housing 10 which may have a compartment 12 within which is positioned a paper towel roll 14. A slot or aperture is formed in the housing through which the towels will pass to the user. An opening 16 is formed in the housing and this opening is aligned with the core 18 of the roll 14.

In this second embodiment of the invention, a roller 40 is rotated when a user pulls a towel through the slot or aperture formed in the housing. The pulling force exerted on the towel drives the roller 40 which is connected by a shaft 42 to a large diameter pulley 44. A belt 46 connects pulley 44 to a smaller diameter pulley 48 which rotates a fan 50. The rotation of the fan blows air through the core 18 of the paper towel roll 14 and dispenses deodorizing air into the surrounding area.

In lieu of the described pulley and belt drive for the fan 50, other mechanical drive mechanisms known to those skilled in the art may be used.

Of particular importance in the invention is the combination of a paper towel roll and a suitable deodorant which is associated with the core of the roll. The user need do nothing other than require a towel from the roll, either through operation of the infrared sensor or the manual switch 34, and such act by the user automatically dispenses deodorized air into the surrounding area. Whenever the paper towel roll is replaced after it is used, simultaneously a new source of deodorant will be supplied as the core of the roll will include the deodorant, either in impregnated form or as separate granules or a cake positioned in the core.

Whereas preferred forms of the invention have been shown and described herein, it should be realized that there may be many modifications, substitutions and alterations thereto.

What is claimed is:

1. A deodorizing paper towel dispenser including a housing, a paper towel roll mounted for rotation within the housing, a roller contacting an exterior portion of the paper towel roll wherein the roller is rotatively driven when the towel is dispensed, a fan operably connected to the roller so that the roller drives the fan, the paper towel roll including a generally hollow core, a deodorant associated with said core, the fan positioned to pass air through the paper towel roll core, an opening in said housing for air passing through said core, said fan being driven by the roller such that said fan and said paper towel roll rotate concurrently.

2. The deodorizing paper towel dispenser of claim 1 wherein said deodorant is impregnated within said paper towel roll core.

3. The deodorizing paper towel dispenser of claim 1 wherein said deodorant is physically positioned within said paper towel roll core.

4. The deodorizing paper towel dispenser of claim 1 wherein the fan is operably connected to the roller by a mechanical connection.

5. The deodorizing paper towel dispenser of claim 4 wherein the mechanical connection comprises a pulley and belt drive.

\* \* \* \* \*